(12) United States Patent
Collins (10) Patent No.: US 6,782,073 B2
(45) Date of Patent: Aug. 24, 2004

(54) PLANNING SYSTEM FOR CONVERGENT RADIATION TREATMENT

(75) Inventor: William F. Collins, Clayton, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 51 days.

(21) Appl. No.: 10/252,980

(22) Filed: Sep. 23, 2002

(65) Prior Publication Data

US 2003/0206611 A1 Nov. 6, 2003

Related U.S. Application Data

(60) Provisional application No. 60/377,352, filed on May 1, 2002.

(51) Int. Cl.[7] .................................................. A61N 5/10
(52) U.S. Cl. ........................... 378/65; 378/84; 600/431
(58) Field of Search .............................. 378/64, 65, 84, 378/145, 147; 600/407, 411, 420, 427, 431, 436, 439

(56) References Cited

U.S. PATENT DOCUMENTS

| | | |
|---|---|---|
| 1,865,441 A | 7/1932 | Mutscheller |
| 2,557,662 A | 6/1951 | Kirkpatrick |
| 5,604,782 A | 2/1997 | Cash, Jr. |
| 6,125,295 A | 9/2000 | Cash, Jr. et al. |
| 6,195,410 B1 | 2/2001 | Cash, Jr. |
| 6,359,963 B1 | 3/2002 | Cash |
| 6,366,801 B1 | 4/2002 | Cash, Jr. et al. |
| 6,389,100 B1 * | 5/2002 | Verman et al. ............... 378/84 |
| 2001/0043667 A1 | 11/2001 | Antonell et al. |

OTHER PUBLICATIONS

"Highly Oriented Pyrolytic Graphite", download from http://www.win.ne.ip~techno/e_HOPG.html on Jul. 29, 2002, 1pg.

"Overview of Cancer and Radiation Therapy", download from http://www.vetradtherapy.com/overview.html on Jul. 24, 2002, 6pgs.

* cited by examiner

Primary Examiner—David V. Bruce
Assistant Examiner—Courtney Thomas

(57) ABSTRACT

A system includes determination of a treatment plan for delivering convergent radiation to a target based at least on a decrease in intensity of the convergent radiation due to material intercepted by the convergent radiation prior to reaching the target and on an increase in intensity of the convergent radiation due to a geometry of the convergent radiation. Some aspects include determination of a dose enhancement at the target over time due to contrast agent located at the target, wherein the determination of the treatment plan is based at least on the dose enhancement over time.

26 Claims, 7 Drawing Sheets

PLANNING SYSTEM FOR CONVERGENT RADIATION TREATMENT

CROSS-REFERENCE TO RELATED APPLICATIONS

This application claims priority to U.S. Provisional Application No. 60/377,352, filed May 1, 2002 and entitled "System and Method of Focused Orthovoltage Technology for Radiotherapy".

BACKGROUND

1. Field

The present invention relates generally to medical treatment using convergent radiation, and more particularly to systems for planning and/or delivering such treatment.

2. Description

Conventional radiation treatment typically involves directing a radiation beam at a tumor located within a patient. The radiation beam is intended to deliver a predetermined dose of treatment radiation to the tumor according to an established treatment plan. The goal of such treatment is to kill tumor cells through ionizations caused by the radiation.

Healthy tissue and organs are often in the treatment path of the radiation beam during radiation treatment. The healthy tissue and organs must be taken into account when determining a treatment plan. Specifically, the treatment plan must strike a balance between the need to minimize damage to healthy tissue and organs and the need to ensure that the tumor receives an adequately high dose of radiation. In this regard, cure rates for many tumors are a sensitive function of the radiation dose they receive.

It is therefore desirable to design treatment plans that maximize radiation delivered to a target while minimizing radiation delivered to healthy tissue. In conventional radiation treatment systems, a linear accelerator generates a divergent beam of photons having energies in excess of 1 MeV and the beam is directed toward a target within a patient. A conventional treatment plan may call for shaping the beam with beam shaping devices to conform to the target and to avoid healthy tissue. A dose delivered by a conventional megavoltage system reaches a maximum at a tissue depth that depends on the energy of the delivered photons. Accordingly, conventional treatment plans also call for photons having energies corresponding to the depth of the target.

A kilovoltage radiation treatment system such as those described in U.S. Pat. No. 6,366,801 to Cash et al uses a radiation source which produces a divergent beam of traditional medical x-rays having energies in the 50 to 150 keV range and focuses the beam on a target using a lens designed for this purpose. Conventional planning systems such as those described above are not suitable for these treatment systems because the characteristics of the focused beam are quite different from those of conventional megavoltage radiation. For example, the focused beam follows a convergent, rather than a divergent, path. Also, while absorption of the megavoltage radiation may be considered dependent primarily on the density of tissue through which it passes, absorption of the focused beam is highly dependent on tissue composition.

Moreover, as described in Cash, kilovoltage radiation may be used to irradiate a tumor that has been injected with a contrast agent composed of heavy elements. The tumor thereby receives a larger radiation dose than it would have received without use of the contrast agent. Contrast agents are not commonly used in conjunction with megavoltage radiation treatment, therefore conventional treatment planning systems are also not suitable for planning treatments in which tumors injected with contrast agent are irradiated by kilovoltage radiation.

SUMMARY

To address at least the foregoing, some embodiments of the present invention provide a system, method, apparatus, and means to determine a treatment plan for delivering convergent radiation to a target based at least on a decrease in intensity of the convergent radiation due to material intercepted by the convergent radiation prior to reaching the target and on an increase in intensity of the convergent radiation due to a geometry of the convergent radiation. Some aspects include determination of a dose enhancement at the target over time due to contrast agent located at the target, wherein the determination of the treatment plan is based at least on the dose enhancement over time.

In other aspects, a system is provided having a radiation source for emitting radiation, a radiation-focusing lens for substantially focusing the radiation on a target, and a processor for determining a treatment plan for delivering convergent radiation to a target based at least on a decrease in intensity of the convergent radiation due to material intercepted by the convergent radiation prior to reaching the target and on an increase in intensity of the convergent radiation due to a geometry of the convergent radiation. According to some aspects, the system further includes a contrast agent delivery unit for placing contrast agent at the target, and an imaging system for generating data representing a decrease in the contrast agent at the target over time, wherein the determination of the dose enhancement over time includes a determination of a decrease in the contrast agent at the target over time based at least on the data representing the decrease in the contrast agent.

Some aspects of the invention include determination of an energy distribution profile of radiation convergent on a target by a radiation-focusing lens, acquisition of data representing material between the radiation-focusing lens and the target, determination of a decrease in intensity of the convergent radiation at the target due to the material and based on the energy distribution profile, determination of an increase in intensity of the convergent radiation at the target due to a geometry of the convergent radiation, and determination of a treatment plan based at least on the decrease in intensity of the convergent radiation at the target due to the material and the increase in intensity of the convergent radiation at the target due to the geometry of the convergent radiation. Further to these aspects, also provided may be determination of a decrease in contrast agent at the target over time, and determination of a dose enhancement function based at least on the decrease in the contrast agent at the target over time, wherein the treatment plan is determined based at least on the dose enhancement function.

The present invention is not limited to the disclosed embodiments, however, as those of ordinary skill in the art can readily adapt the teachings of the present invention to create other embodiments and applications.

BRIEF DESCRIPTION OF THE DRAWINGS

The exact nature of this invention, as well as its objects and advantages, will become readily apparent from consideration of the following specification as illustrated in the accompanying drawings, in which like reference numerals designate like parts, and wherein.

DETAILED DESCRIPTION

The following description is provided to enable any person of ordinary skill in the art to make and use the invention and sets forth the best modes contemplated by the inventor for carrying out the invention. Various modifications, however, will remain readily apparent to those in the art.

Figure 1:
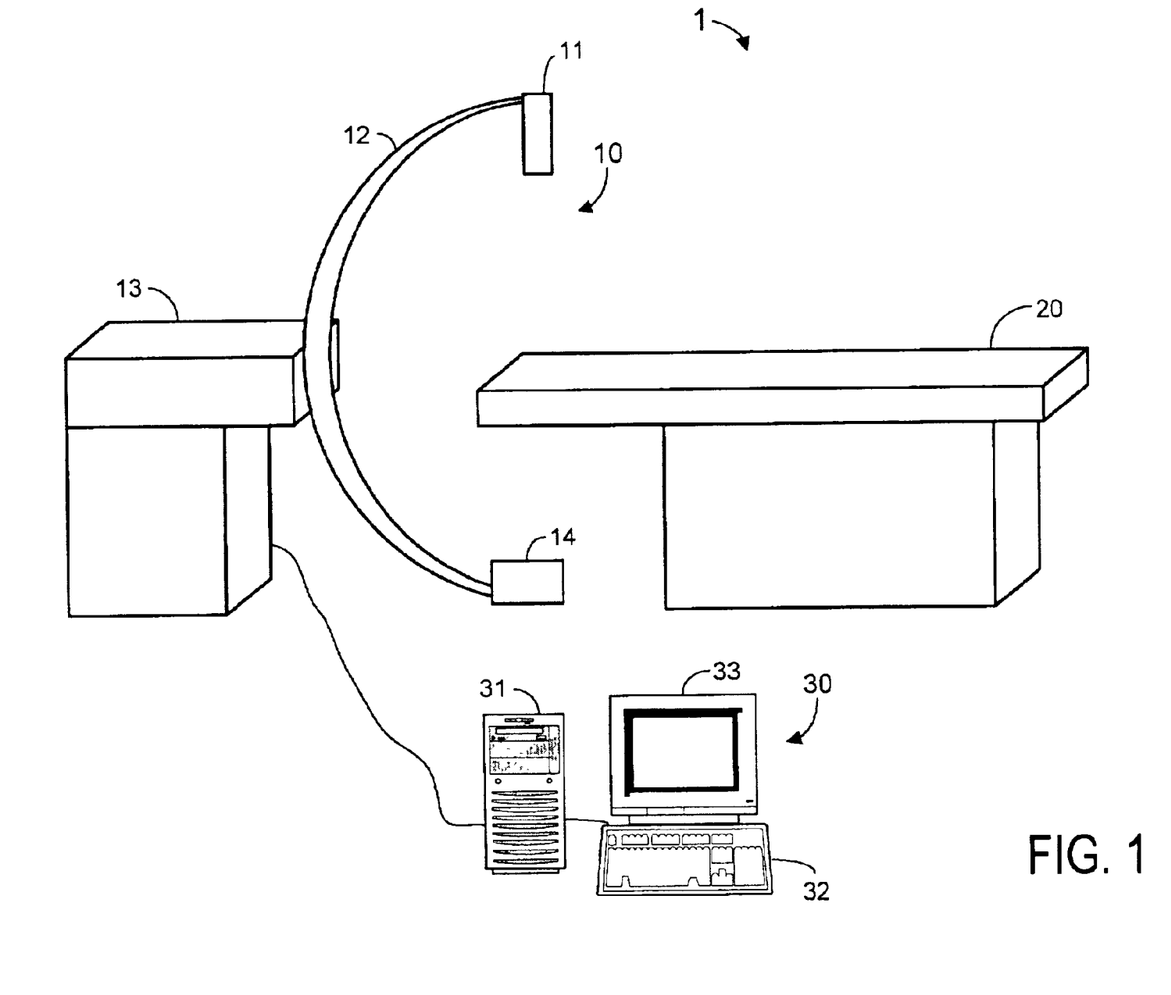
FIG. 1 is a diagram illustrating a radiation treatment room according to some embodiments of the present invention.

FIG. 1 illustrates radiation treatment room 1 pursuant to some embodiments of the present invention. Radiation treatment room 1 includes kilovoltage radiation treatment unit 10, treatment table 20 and operator station 30. The elements of radiation treatment room 1 may be used to determine a treatment plan and/or to deliver kilovoltage radiation to a patient according to a treatment plan. In this regard, kilovoltage radiation refers herein to any radiation having energies ranging from 50 to 150 keV. However, it should be noted that some embodiments of the present invention may be used in conjunction with any convergent radiation beam.

Treatment unit 10 is used to deliver treatment radiation to a treatment area and includes treatment head 11, c-arm 12, base 13 and imaging system 14. Treatment head 11 includes a beam-emitting device such as an x-ray tube for emitting kilovoltage radiation used during calibration and/or treatment. The radiation may comprise electron, photon or any other type of radiation. Treatment head 11 also includes a cylinder in which are disposed optics such as a focusing lens for optically processing the emitted radiation. Treatment head 11 will be described in more detail below with respect to FIG. 2.

C-arm 12 is slidably mounted on base 13 and can therefore be moved in order to change the position of treatment head 11 with respect to table 20. In some embodiments, base 13 also includes a high-voltage generator for supplying power used by treatment head 11 to generate kilovoltage radiation. Many c-arm/base configurations may be used in conjunction with some embodiments of the present invention, including configurations in which base 13 is rotatably mounted to a ceiling of room 1, configurations in which one c-arm is slidably mounted on another c-arm, and configurations incorporating multiple independent c-arms.

Examples of c-arm kilovoltage radiation units include Siemens SIREMOBIL™, MULTISTAR™, BICOR™ and POLYSTAR™ units as well as other units designed to perform tomography and/or angiography. These units are often less bulky and less costly than megavoltage radiation systems. Of course, any system for delivering a convergent radiation beam may be used in conjunction with some embodiments of the present invention.

Imaging system 14 produces an image based on the radiation emitted by treatment head 11. The image reflects the attenuative properties of material located between treatment head 11 and imaging system 14 while the radiation is emitted. Imaging system 14 may comprise an image intensifier and a camera. An image intensifier is a vacuum tube that converts x-rays to visible light, which is then detected by the camera to produce an image. Imaging system 14 may also comprise a flat-panel imaging system that uses a scintillator and silicon sensor elements or direct x-ray conversion detectors to produce an image based on received radiation.

During radiation treatment, a patient is placed on treatment table 20 in order to position a target between treatment head 11 and imaging system 14. Accordingly, table 20 may comprise mechanical systems for moving itself with respect to unit 10.

Operator station 30 includes a processor 31 in communication with an input device such as keyboard 32 and an operator display 33. An operator may operate operator station 30 to plan a radiation treatment according to some embodiments of the invention. Operator station 30 may also be operated to deliver radiation in accordance with a treatment plan. Operator station 30 may be located apart from treatment unit 10, such as in a different room, in order to protect the operator from radiation. It should be noted, however, that kilovoltage radiation treatment does not require protective measures to the extent of those taken during megavoltage radiation therapy, resulting in less costly therapy.

Processor 31 may store processor-executable process steps according to some embodiments of the present invention. In some aspects, the process steps are executed by operator station 30, treatment unit 10, and/or another device to determine a treatment plan for delivering convergent radiation to a target based at least on a decrease in intensity of the convergent radiation due to material intercepted by the convergent radiation prior to reaching the target and on an increase in intensity of the convergent radiation due to a geometry of the convergent radiation.

The process steps may also provide determination of an energy distribution profile of radiation convergent on a target by a radiation-focusing lens, acquisition of data representing material between the radiation-focusing lens and the target, determination of a decrease in intensity of the convergent radiation at the target due to the material and based on the energy distribution profile, determination of an increase in intensity of the convergent radiation at the target due to a geometry of the convergent radiation, and determination of a treatment plan based at least on the decrease in intensity of the convergent radiation at the target due to the material and the increase in intensity of the convergent radiation at the target due to the geometry of the convergent radiation.

The above-described steps may also be embodied, in whole or in part, by hardware of processor 31, treatment unit 10, and another device. Of course, each of the devices shown in FIG. 1 may include less or more elements than those shown. In addition, embodiments of the invention are not limited to the devices and/or the environment shown.

Figure 2:
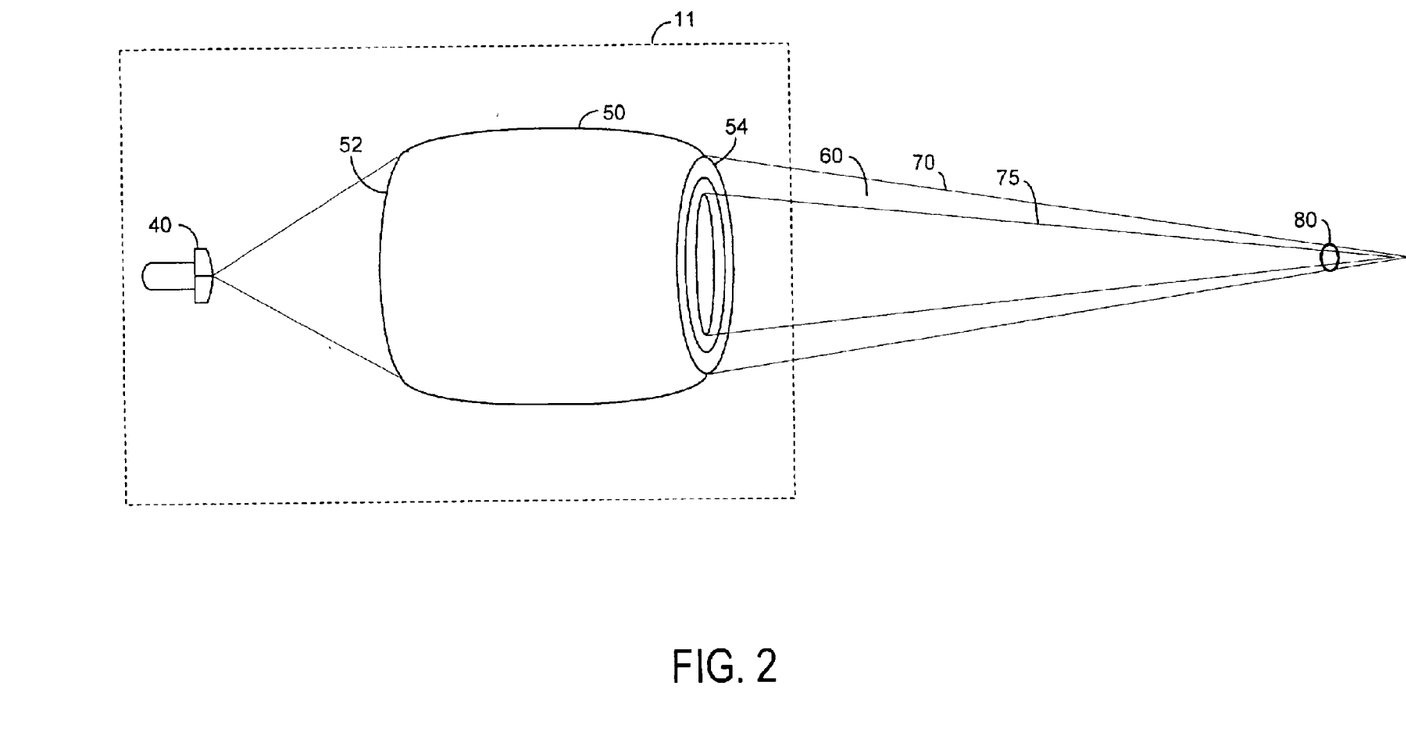
FIG. 2 is a diagram illustrating a radiation-focusing lens according to some embodiments of the present invention.

FIG. 2 is a representative view of elements of treatment head 11 according to some embodiments of the present invention. As shown, treatment head 11 includes x-ray tube 40 and lens 50. In operation, radiation is emitted by x-ray tube 40 toward lens 50. The radiation enters entry surface 52 of lens 50 and some or all of the radiation exits exit surface 54.

Lens 50 may comprise any lens for producing a convergent radiation beam, including those having a shape different from that illustrated. In this regard, lens 50 of FIG. 2 comprises strips of reflective material arranged in the form of several thin barrels nested around a central axis but separated from one another. Each "barrel" is separated from adjacent "barrels" by Plexiglas or another optically neutral substrate. Lens 50 may also comprise any other lens such as radiation-focusing described in U.S. Pat. No. 6,359,963 to Cash, in U.S. Pat. No. 5,604,782 to Cash, Jr., in U.S. Pat. No. 6,606,371 to Antonell et al., and/or elsewhere in currently or hereafter-known art.

Highly Oriented Pyrolitic Graphite (HOPG) may be used as the reflective material of lens 50. HOPG consists of planes of carbon atoms that are highly oriented toward one another. In the ideal variant, these planes are parallel to one another.

By virtue of its composition, shape and construction and of properties of the emitted radiation, lens 50 directs the radiation along path 60. Geometrically, path 60 comprises the volume between outer cone surface 70 and inner cone surface 75.

Lens 50 operates to substantially focus all or a portion of the radiation exiting from exit surface 54 on target 80. Target 80 may be a point in space or a larger area. In some embodiments of lens 50, target 80 is approximately 1 cm in diameter. According to the FIG. 2 embodiment, target 80 is spaced from an exit surface of lens 50 by a distance determined by the composition, shape and construction of lens 50 as well as by characteristics of the emitted radiation.

Path 60 does not terminate at the illustrated point of convergence. Rather, path 60 continues thereafter, becoming further attenuated and unfocused as its distance from lens 50 increases. In some embodiments, this divergence of path 60 roughly mirrors its convergence from lens 50 after the point of convergence. It should be noted that target 80 may be located at the point of convergence.

It should be noted that treatment head 11 may also include beam shaping devices such as one or more jaws, collimators, reticles and apertures. By changing the shape of path 60, these devices may cause a change in the shape and/or position of target 80. The devices may be placed between lens 50 and target 80 and/or between x-ray tube 40 and lens 50.

Figure 3:
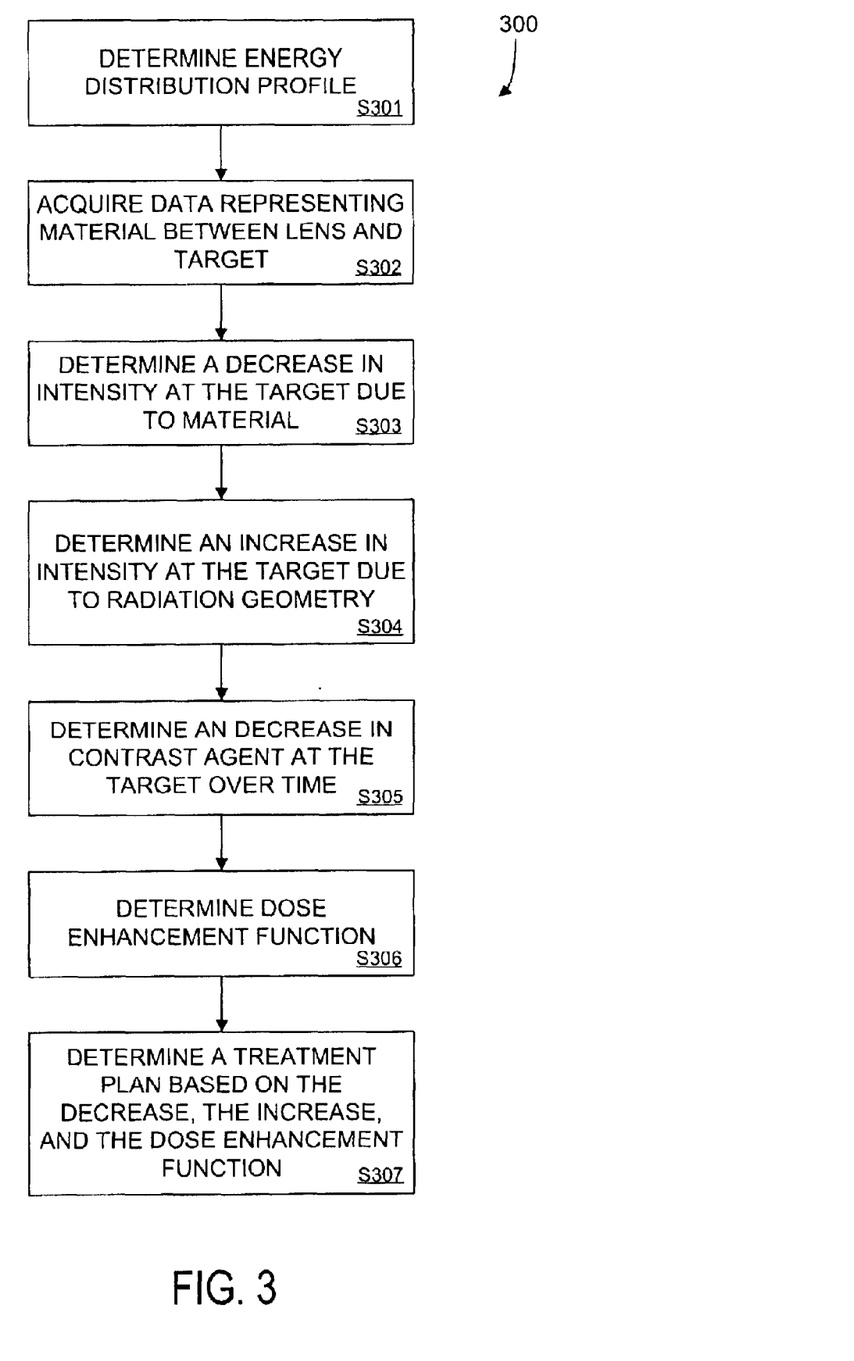
FIG. 3 comprises a flow diagram illustrating process steps according to some embodiments of the present invention.

FIG. 3 comprises a flow diagram of process steps 300 to determine a treatment plan according to some embodiments of the invention. Process steps 300 may be embodied by hardware, firmware and/or software of processor 31, treatment unit 10, and/or another device.

Process steps 300 begin at step S301, in which an energy distribution profile of radiation exiting from exit surface 52 is determined. In this regard, lens 50 may selectively filter and distribute photons received from x-ray tube 40 along radiation path 60 according to their respective energies. The filtering and distribution may be dependent upon the Bragg angle of lens 50. Generally, each point within path 60 may be associated with a specific photon energy. The specific energy associated with a point may be represented in some embodiments by a profile. The profile may be represented by a mathematical function of the energy of radiation emitted by x-ray tube 40 and a location of the point in space.

Figure 4A:
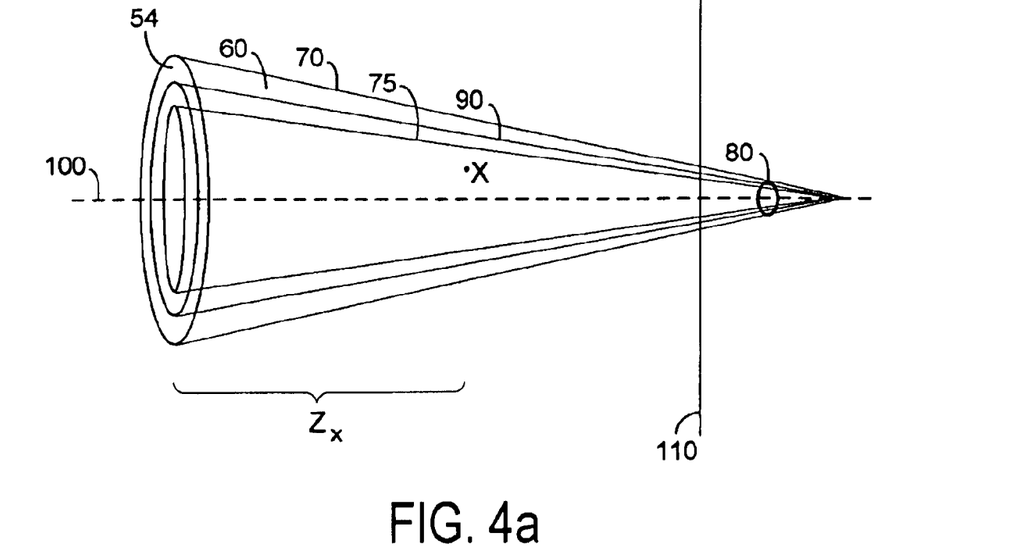
FIGS. 4a and 4b are diagrams illustrating an energy distribution profile according to some embodiments of the present invention.
Figure 4B:
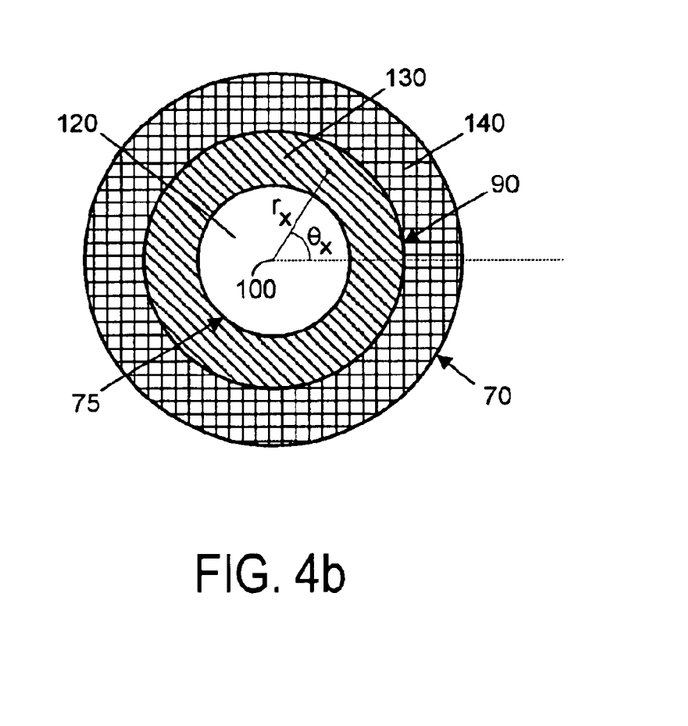

FIGS. 4a and 4b graphically illustrate the above-described energy distribution profile associated with a 60 keV radiation beam emitted by x-ray tube 40 toward lens 50. Radiation beams having other energies may be emitted by x-ray tube 40 according to some embodiments. These beams may be associated with energy distribution profiles identical to or different from the profile illustrated in FIGS. 4a and 4b. Generally, an energy distribution profile of radiation emitted by lens 50 may be a function of one or more of 1) a type of radiation incident to lens 50, 2) an energy distribution of radiation incident to lens 50, 3) a shape of lens 50, 4) a composition of lens 50, and 5) other factors.

FIG. 4a shows exit surface 54, path 60 and target 80. It should be noted that path 60 of FIG. 4a includes cone surface 90 between surfaces 70 and 75. Cone surface 90 was not illustrated in FIG. 2 because cone surface 90 does not define boundaries of path 60. Rather, cone surface 90 is a boundary between two volumes in which photons of two different energies are respectively distributed. This distribution will be described in more detail with respect to FIG. 4b.

Continuing with FIG. 4a, central axis 100 of path 60 may be used to define a coordinate associated with a point within path 60. For example, point X represents an infinitesimal area within path 60 that is associated with the "Z" coordinate $Z_X$. Skin surface 110 is shown to illustrate that an energy distribution profile according to some embodiments is not affected by material placed between exit surface 54 and target 80.

FIG. 4b is a cross section of path 60 with a plane perpendicular to central axis 100. In the present example, radiation emitted from exit surface 54 does not enter area 120. Area 120 is bordered by a circular portion of inner surface 75, which is in turn surrounded by area 130. Similarly, area 130 is bordered by a circular portion of cone surface 90, which is surrounded by area 140, which is in turn bordered by a circular portion of outer surface 70.

According to the present embodiment, cone surface 90 lies midway between outer surface 70 and inner surface 75 in any plane perpendicular to central axis 100. Therefore, the circular portion of cone surface 90 shown in FIG. 4b is midway between the circular portion of inner surface 75 and the circular portion of outer surface 70. This relationship holds for each cross section of path 60 with a plane perpendicular to central axis 100, even though the circular portions will be smaller in cross sections taken closer to target 80, and will be larger in cross sections taken closer to exit surface 54.

Within each of such cross sections, positions located between the circular portion of cone surface 90 and the circular portion of inner surface 75 are associated with 57 keV photon energies. On the other hand, positions located between the circular portion of outer surface 70 and the circular portion of cone surface 90 are associated with 63 keV photon energies. In the present example, we assume radiation sources with energies higher than 63 keV and lens geometries that result in emitted radiation having a center energy (e.g., 60 keV) plus or minus some spread (e.g., 3 keV).

Point X is located within the illustrated cross section. Accordingly, the Z coordinate of each point in the cross section is $Z_X$. A location of point X is further defined by its distance ($r_x$) from central axis 100 and its rotation ($\theta_x$) from the illustrated θ=0 reference line. Each position within path 60 may therefore be represented by a (r, θ, z) coordinate.

The energy distribution profile of FIGS. 4a and 4b may be determined in step S301 by mathematical modeling, such as Monte Carlo simulation, of radiation emitted by lens 50 in response to 60 keV radiation emitted by x-ray tube 40, when, for example, x-ray tube 40 is operated at 120 keV. The profile may also be determined by actually delivering the 60 keV radiation to lens 50 and by measuring photon energies at multiple points within path 60, and/or by other currently- or hereafter-known methods. The energy distribution profile illustrated in FIGS. 4a and 4b may be represented as a function of r, θ and Z. A more complete profile may be determined by determining energy distribution profiles for other photon energies delivered by x-ray tube 40. In this latter case, the energy distribution profile may be represented as a function of r, θ, Z and the radiation energy emitted by x-ray tube 40.

According to process steps 300, data representing material between lens 50 and target 80 is acquired in step S302. Such data typically represents portions of a patient's body that would lie within path 60 during treatment. The data may be obtained in step S302 using a computed tomography (CT) scanner, such as CT scanner 150 of FIG. 5.

Figure 5:
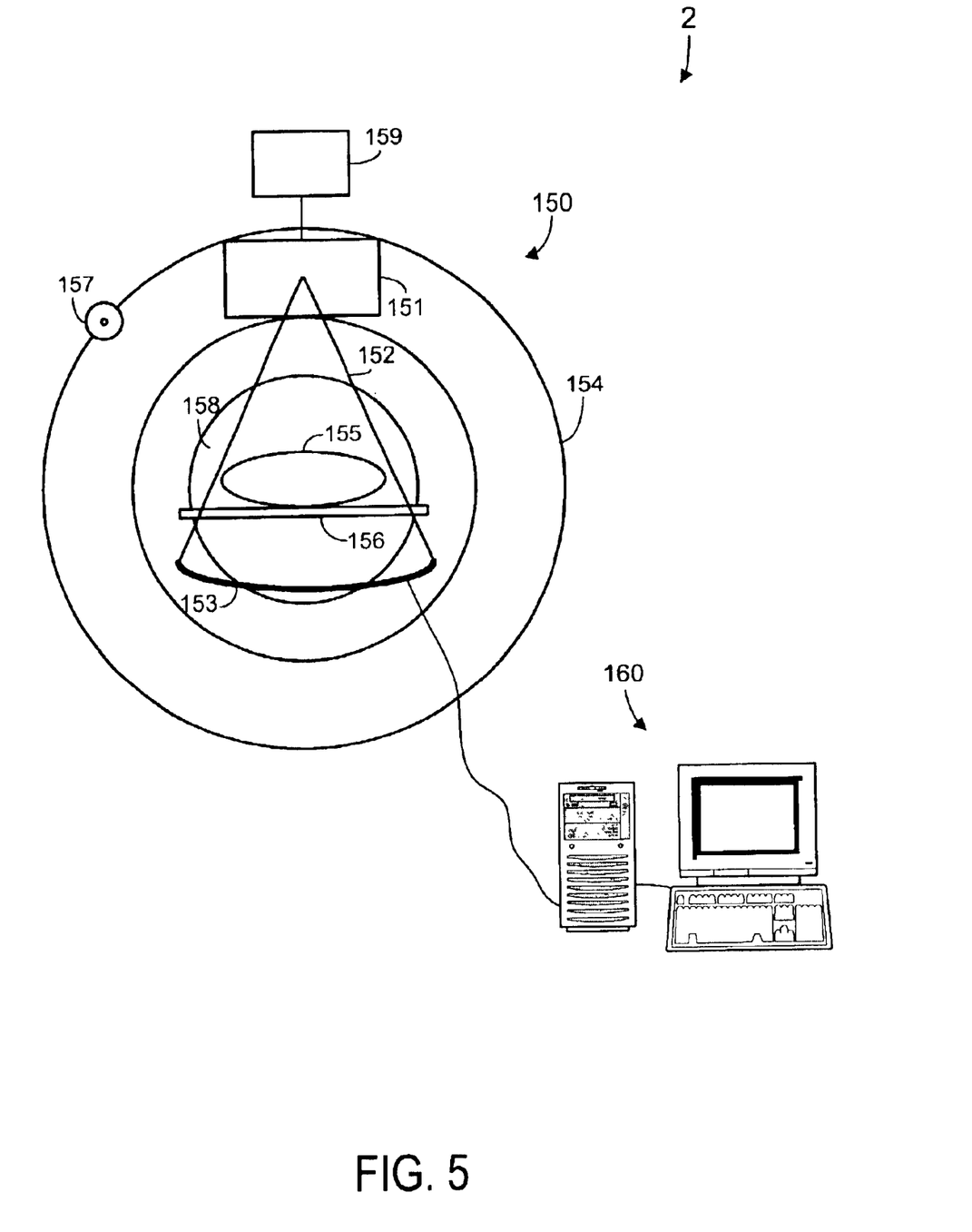
FIG. 5 is a view of a diagnostic computed tomography (CT) room.

CT scanner 150 is located in CT room 2 and may be operated prior to step S301 to obtain data for diagnosing a patient and/or for planning radiation treatment. In this regard, the data may be acquired in step S302 merely by obtaining previously-acquired data from a storage device. CT scanner 150 includes x-ray source 151 for emitting fan-shaped x-ray beam 152 toward radiation receiver 153. Both x-ray source 151 and radiation receiver 153 are mounted on ring 154 such that they may be rotated through 360 degrees while maintaining the physical relationship therebetween. Patient 155 lies on patient bed 156 in order to acquire data representing portions of the patient's body that may lie within path 60 during treatment. Next, x-ray source 151 and receiver 153 are rotated by rotation drive 157 around a measurement field 158 in which patient 155 lies.

During this rotation, x-ray source 151 is powered by high-voltage generator 159 to transmit radiation toward receiver 153. At predetermined rotational angle positions, receiver 153 produces sets of data and the sets of data are transmitted to computer system 160. Computer system 160 calculates attenuation coefficients (Hounsfield numbers) of predetermined points from the registered data sets to generate data representing portions of patient 155 that may lie within path 60 during treatment. Accordingly, the data represents the attenuative properties of tissues at each point of the represented portions.

The data acquired in step S302 may be used with the energy distribution profile in step S303 to determine a decrease in intensity at the target due to material lying between the lens and the target. In this regard, radiation is attenuated at a particular point based on attenuative properties of material located at the particular point and on the energy of the radiation. This attenuation is described by the equation:

$$I/I_0 = e^{-\mu \rho z},$$

where $I_o$ represents an intensity of radiation incident to the point, I represents an intensity of radiation exiting the point, μ represents the material's mass attenuation coefficient, ρ represents a density of the material, and z represents a distance between the incidence and the exit of the radiation. It should be noted that μ for a particular material differs for different energies of incident radiation. For example, μ for human skeletal muscle is 0.205 cm²/gm in a case of 60 keV incident x-ray radiation, but is 0.182 cm²/gm in a vase of 80 keV incident x-ray radiation. These values may be obtained by referring to any readily-available table of mass attenuation coefficients.

Figure 6:
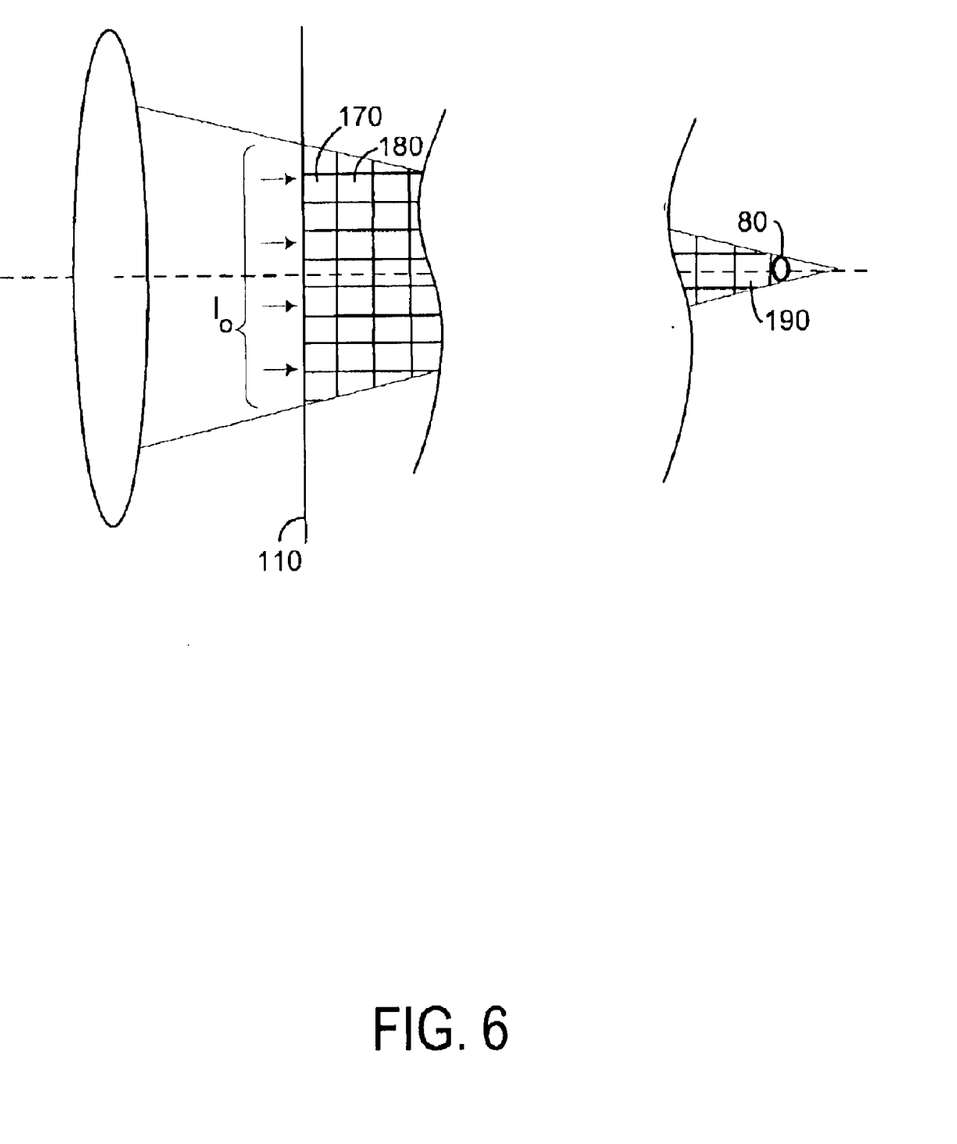
FIG. 6 is a diagram illustrating determination of a decrease in intensity of focused radiation due to material between a lens and a target according to some embodiments of the present invention.

FIG. 6 illustrates a specific example of determining the decrease in intensity at the target in step S303. As shown, material lying between lens 50 and target 80 has been segmented into many small volumes. The data acquired in step S302 is used to determine a value of ρ for each volume. In a case that a specific volume is composed of several different materials, the ρ value determined for the specific volume may be based on the ρ value of each different material. In some embodiments, the ρ value for the specific volume is based on the ρ value of each different material, weighted according to percentage composition of each different material within the specific volume. It should be noted that the volumes of FIG. 6 can be of any size, and that the volumes may be equally- or differently-sized with respect to one another. Moreover, the material segmented into volumes may also include material, such as air, lying between exit surface 54 and skin surface 110.

Each volume is also associated with an energy value. The energy value is determined based on the energy distribution profile. More specifically, the location of a volume within path 60 is determined based on the data acquired in step S302 and a data model of path 60. Next, an energy associated with the location is determined from the energy distribution profile. For volumes of non-infinitesimal size, the energy distribution profile may associate the location of the volume with several energies. The energy associated with such volumes may be a composite of the several energies.

In addition, each volume is associated with a μ value. The μ value associated with a volume may be determined by identifying an appropriate table of mass attenuation coefficients based on the radiation energy associated with the volume, by using the data acquired in step S302 to identify the material within the volume and by locating a μ value associated with the material in the table. As described above, a volume may be composed of several different materials and may be associated with several different energies. Accordingly, the μ value of the volume may be determined based on several μ values, each of which corresponds to one of the materials and energies.

The μ value of the volume may be estimated directly from the data acquired in step S302. In this regard, the data comprises a Hounsfield Unit for each point represented by the data. The μ value of the volume may therefore be determined using the relation: Hounsfield Unit$_{volume}$= $[\mu_{volume} - \mu_{water}]/\mu_{water}$.

As shown in FIG. 6, radiation of energy $I_o$ is incident upon skin surface 110. In some examples of step S303, it is assumed that the intensity of radiation is split equally among the volumes that include skin surface 110. Using the above equation, the intensity of radiation exiting each volume equals $I_o e^{-\mu \rho z}/V$, wherein V is the number of volumes that include skin surface 110 and the values of μ, ρ and z are specific to each volume. It should be noted that the intensity incident upon the V volumes need not be uniform, and is based on a shape of path 60 at skin surface 110.

According to the FIG. 6 example, the exit surface of volume 170 is identical to the entry surface of volume 180. Consequently, the calculated intensity of radiation exiting volume 170 is assumed to be equal to the intensity of radiation entering volume 180. As such, the intensity exiting volume 180 is governed by the equation:

$$I = (I_o e^{-\mu \rho z (volume\ 170)}/V) e^{-\mu \rho z (volume\ 180)}$$

The intensity of radiation exiting each volume of material lying between lens 50 and target 80 may continue to be determined as described above until the intensity of radiation exiting volume 190 is determined. According to the present example, the intensity of radiation exiting volume 190 is equal to the intensity of radiation entering target 80. As shown above, the intensity of radiation entering target 80 will be expressed as $CI_o$, where C is a constant less than 1. Therefore, according to some embodiments, the decrease in intensity at target 80 due to material lying between lens 50 and target 80 may be expressed as (1-C).

An increase in intensity of the radiation emitted from exit surface 54 due to a geometry of the radiation is determined in step S304. Generally, the cross sectional area of path 60 decreases from lens 50 to target 80. Since the total energy passing through any cross-sectional area at any given time is constant, the energy per unit area increases from lens 50 to target 80. Accordingly, the intensity of the radiation increases from lens 50 to target 80.

Figure 7:
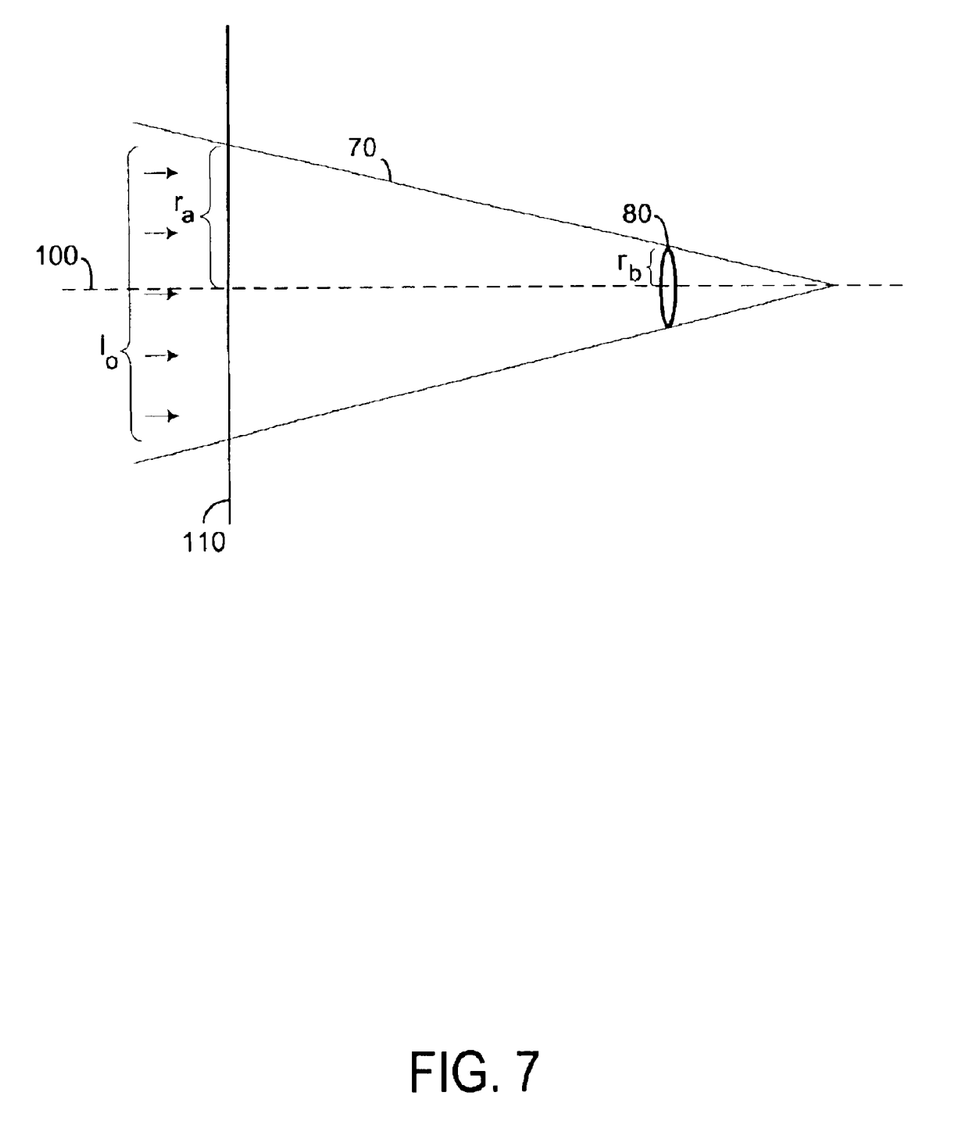
FIG. 7 is a diagram illustrating determination of an increase in intensity of focused radiation due to a geometry of the focused radiation according to some embodiments of the present invention.

FIG. 7 is a diagram for illustrating the step S304 determination. As shown, distance $r_a$ represents a distance from central axis 100 to outer surface 70 at skin surface 110. Distance $r_b$ represents a distance from central axis 100 to outer surface 70 as measured at target 80. Each of these distances may be determined from experimentally or calculated data representing the geometry of outer surface 70 and the data acquired in step S302, which provides a distance between target 80 and skin surface 110. For the geometry of the present example, the intensity I at target 80 can be expressed as follows:

$$I=I_o r_a^2/r_b^2.$$

Of course, other equations for I may be appropriate for other beam geometries.

After step S304, an intensity at target 80 due to material intercepted by the convergent radiation prior to reaching target 80 and due to a geometry of the radiation can be expressed by the equation:

$$I=I_o(C+r_a^2/r_b^2).$$

Therefore, an intensity at target 80 for a given $I_o$ may be determined. Conversely, an $I_o$ required for a desired I at target 80 may be determined from the equation:

$$I_o=I/(C+r_a^2/r_b^2).$$

The desired I may be determined based on a desired dose and a mass of target 80 using the formula I=dose*mass. It should be noted that the calculation of C as described above is dependent upon the energies and energy distribution of the incident radiation. Accordingly, the previous two equations may not be applicable to all radiation energies and/or distributions.

In step S305, a decrease in contrast agent at target 80 over time is determined. Step S305 is used in the context of a treatment plan involving the injection of a contrast agent comprising high atomic number material into target 80. Such treatment attempts to increase the photoelectric absorption of radiation by cells located at target 80. In this regard, an increase in photoelectric absorption results in increased cellular damage.

The contrast agent used in step S305 may be selected based on currently- or hereafter-known techniques. Generally, the selection may consider the atomic number of the agent, the distance of target 80 from skin surface 110, and the energy of the treatment radiation. Some possible materials include iodine, Gadolinium, gold and tin. The contrast agent may comprise several materials, at least one of which is characterized by a high atomic number.

The contrast agent may be injected directly into target 80 or provided intravenously under control of a delivery unit of processor 31. In order to determine a decrease in the contrast agent over time, CT scanner 150 is used to acquire data representing target 80 at regular time intervals following delivery of the contrast agent to target 80. A function relating time to a percentage of contrast agent by weight within target 80 can then be determined based on the acquired data. Due to patient blood flow, the function should generally show an overall decrease in the percentage of contrast agent within target 80 over time.

Next, in step S306, a dose enhancement function is determined. The dose enhancement function reflects an increase in the damaging effect of radiation at target 80 due to the contrast agent. The dose enhancement function can be used to determine dose enhancement based on photon energy and contrast agent concentration. For one particular photon energy and under particular conditions described in the aforementioned patent to Cash, the dose enhancement function may be determined by the equation:

$$d/d_0=1+1.3p,$$

wherein d represents the dose experienced at target 80 using a contrast agent, $d_0$ represents the dose experienced at target 80 without using the contrast agent, and p equals a percentage of contrast agent within target 80 by weight. Since p was determined as a function of time in step S305, the function may be substituted for p in the foregoing equation to create a new function $d/d_0=1+1.3 f(t)$ that specifies a dose enhancement at target 80 over time.

In a second example, the dose enhancement function is determined by acquiring CT data of target 80 while target 80 is injected with contrast agent at time $t_0$. The dose enhancement at a photon energy between 40 to 80 keV may be given by 1+0.0025H, where H is a Hounsfield Unit of target 80 read directly from the CT data. CT data of target 80 is then periodically acquired as a concentration of contrast agent within target 80 decreases. Dose enhancement values corresponding to each of the periodically-acquired CT data are determined, resulting in a table of various dose enhancement values and corresponding time values>$t_0$. The table of values may then be used to determine a dose enhancement function $d/d_0=f(t)$ for the particular photon energy. Some embodiments of this second example do not require the determination of step S305.

A treatment plan is determined in step S307 based on the decrease, increase and function respectively determined in steps S303, S304 and S306. In some embodiments using the dose enhancement function of the second example above, an intensity of incident radiation $I_o$ required to deposit a dose equal to I/m is given by:

$$I_o=[I/(C+r_a^2/r_b^2)]f(t),$$

wherein m is the mass of target 80. It should be noted that since d=I/m, $d/d_0=f(t)=I/I_o$.

Those in the art will appreciate that various adaptations and modifications of the above-described embodiments can be configured without departing from the scope and spirit of the invention. For example, process steps 300 describe only some embodiments of the present invention. Also, some embodiments may account for Compton scattering and/or elastic scattering of emitted radiation between lens 50 and target 80, as well as the photoelectric interactions as described above. More particularly, relative probabilities of each phenomena occurring are well-known functions of x-ray energy, and can therefore be determined based on the energy distribution profile determined in step S301. Therefore, it is to be understood that, within the scope of the appended claims, the invention may be practiced other than as specifically described herein.

What is claimed is:

1. A method comprising:
   determining a treatment plan for delivering convergent radiation to a target based at least on a decrease in intensity of the convergent radiation due to material intercepted by the convergent radiation prior to reaching the target and on an increase in intensity of the convergent radiation due to a geometry of the convergent radiation.

2. A method according to claim 1, further comprising:
   determining the decrease in intensity of the convergent radiation due to the material.

3. A method according to claim 2, wherein the step of determining the decrease in intensity of the convergent radiation comprises:
   determining an energy distribution profile of the convergent radiation; and
   determining the decrease based at least on the energy distribution profile.

4. A method according to claim 2, wherein the step of determining the decrease in intensity of the convergent radiation comprises:
   determining the decrease in intensity of the convergent radiation based at least on data representing internal portions of a patient.

5. A method according to claim 1, further comprising:
   determining a dose enhancement at the target over time due to contrast agent located at the target,
   wherein the determination of the treatment plan is based at least on the dose enhancement over time.

6. A method according to claim 5, wherein the step of determining the dose enhancement over time comprises determining a decrease in the contrast agent at the target over time.

7. A method according to claim 1, further comprising:
   determining the increase in intensity of the convergent radiation due to the geometry of the convergent radiation.

8. A method according to claim 1, wherein the determining step comprises:
   determining the treatment plan based at least on Compton scattering caused by material intercepted by the convergent radiation prior to reaching the target.

9. A method according to claim 1, wherein the determining step comprises:
   determining the treatment plan based at least on elastic scattering caused by material intercepted by the convergent radiation prior to reaching the target.

10. A method according to claim 1, wherein the determining step comprises:
    determining the treatment plan based at least on photoelectric absorption caused by material intercepted by the convergent radiation prior to reaching the target.

11. A computer-readable medium storing computer-executable process steps, the process steps comprising:
    a step to determine a treatment plan for delivering convergent radiation to a target based at least on a decrease in intensity of the convergent radiation due to material intercepted by the convergent radiation prior to reaching the target and on an increase in intensity of the convergent radiation due to a geometry of the convergent radiation.

12. A medium according to claim 11, the process steps further comprising:
    a step to determine a dose enhancement at the target over time due to contrast agent located at the target,
    wherein the determination of the treatment plan is based at least on the dose enhancement over time.

13. A medium according to claim 12, wherein the step of determining the dose enhancement over time comprises determining a decrease in the contrast agent at the target over time.

14. An apparatus comprising:
    a memory storing processor-executable process steps; and
    a processor in communication with the memory and operative in conjunction with the stored process steps to:
      determine a treatment plan for delivering convergent radiation to a target based at least on a decrease in intensity of the convergent radiation due to material intercepted by the convergent radiation prior to reaching the target and on an increase in intensity of the convergent radiation due to a geometry of the convergent radiation.

15. An apparatus according to claim 14, the processor further operative in conjunction with the stored process steps to:
    determine a dose enhancement at the target over time due to contrast agent located at the target,
    wherein the determination of the treatment plan is based at least on the dose enhancement over time.

16. An apparatus according to claim 15, wherein the determination of the dose enhancement over time comprises determining a decrease in the contrast agent at the target over time.

17. A system comprising:
    a radiation source for emitting radiation;
    a radiation-focusing lens for substantially focusing the radiation on a target; and
    a processor for determining a treatment plan for delivering convergent radiation to a target based at least on a decrease in intensity of the convergent radiation due to material intercepted by the convergent radiation prior to reaching the target and on an increase in intensity of the convergent radiation due to a geometry of the convergent radiation.

18. A system according to claim 17, the processor for determining the decrease in intensity of the convergent radiation due to the material.

19. A system according to claim 18, the processor for determining an energy distribution profile of the convergent radiation, and for
    determining the decrease in intensity of the convergent radiation based at least on the energy distribution profile.

20. A system according to claim 18, further comprising an imaging system for generating data representing material internal to a patient,
    wherein the processor determines the decrease in intensity of the convergent radiation based at least on the data representing material internal the patient.

21. A system according to claim 17, the processor for determining a dose enhancement at the target over time due to contrast agent located at the target, and for determining the treatment plan based at least on the dose enhancement over time.

22. A system according to claim 21, further comprising:
    a contrast agent delivery unit for placing contrast agent at the target; and an imaging system for generating data representing a decrease in the contrast agent at the target over time, wherein the determination of the dose enhancement over time comprises determining a decrease in the contrast agent at the target over time based at least on the data.

23. A method comprising:

determining an energy distribution profile of radiation convergent on a target by a radiation-focusing lens;

acquiring data representing material between the radiation-focusing lens and the target;

determining a decrease in intensity of the convergent radiation at the target due to the material and based on the energy distribution profile;

determining an increase in intensity of the convergent radiation at the target due to a geometry of the convergent radiation; and determining a treatment plan based at least on the decrease in intensity of the convergent radiation at the target due to the material and the increase in intensity of the convergent radiation at the target due to the geometry of the convergent radiation.

24. A method according to claim 23, further comprising:

determining a decrease in contrast agent at the target over time; and determining a dose enhancement function based at least on the decrease in the contrast agent at the target over time, wherein the treatment plan is determined based at least on the dose enhancement function.

25. A computer-readable medium storing computer-executable process steps, the process steps comprising:

a step to determine an energy distribution profile of radiation convergent on a target by a radiation-focusing lens;

a step to acquire data representing material between the radiation-focusing lens and the target;

a step to determine a decrease in intensity of the convergent radiation at the target due to the material and based on the energy distribution profile;

a step to determine an increase in intensity of the convergent radiation at the target due to a geometry of the convergent radiation; and a step to determine a treatment plan based at least on the decrease in intensity of the convergent radiation at the target due to the material and the increase in intensity of the convergent radiation at the target due to the geometry of the convergent radiation.

26. A medium according to claim 25, the process steps further comprising:

a step to determine a decrease in contrast agent at the target over time; and a step to determine a dose enhancement function based at least on the decrease in the contrast agent at the target over time, wherein the treatment plan is determined based at least on the dose enhancement function.

* * * * *